US006835538B1

(12) United States Patent
Lauber et al.

(10) Patent No.: US 6,835,538 B1
(45) Date of Patent: Dec. 28, 2004

(54) METHOD OF GENETIC MODIFICATION OF A WILD TYPE VIRAL SEQUENCE

(75) Inventors: Emmanuelle Lauber, Castanet-Tolosan (FR); Hubert Guilley, Berstett (FR); Ken Richards, Pfulgriesheim (FR); Gérard Jonard, Strasbourg (FR)

(73) Assignee: SES Europe N.V./S.A, Tienen (BE)

( * ) Notice: Subject to any disclaimer, the term of this patent is extended or adjusted under 35 U.S.C. 154(b) by 0 days.

(21) Appl. No.: 09/743,905

(22) PCT Filed: Jul. 9, 1999

(86) PCT No.: PCT/BE99/00089

§ 371 (c)(1),
(2), (4) Date: Apr. 24, 2001

(87) PCT Pub. No.: WO00/03025

PCT Pub. Date: Jan. 20, 2000

(30) Foreign Application Priority Data

Jul. 10, 1998 (FR) .......................................... 98 870159

(51) Int. Cl.[7] ........................... C12Q 1/68; C07H 21/04
(52) U.S. Cl. ........................... 435/6; 435/4; 435/320.1; 435/410; 435/419; 435/440; 435/468; 536/23.1; 536/23.6
(58) Field of Search ................................. 435/4, 6, 440, 435/468, 320.1, 410, 419; 536/23.1, 23.6

(56) References Cited

U.S. PATENT DOCUMENTS 6,297,428 B1 * 10/2001 Guilley et al. .............. 800/280

FOREIGN PATENT DOCUMENTS

| WO | WO 91 13159 | 9/1991 |
| WO | WO 98/07875 | 2/1998 |

OTHER PUBLICATIONS

Bouzoubaa, et al. 1986, Nucleotide sequence of beet necrotic yellow vein virus RNA–2. *J. Gen. Virol.*, 67:1689–1700.

Gilmer, et al., *Efficient Cell–to–Cell Movement of Beet Necrotic Yellow Vein Virus Requires 3' Proximal Genes Located on RNA 2*, VIROLOGY 189, pp 40–47.

Xu, et al. *Genetically engineered resistance to potato virus X in four commerical potato cultivars.* Plant Cell Reports, Vo. 15 1995. pp 91–96.

Seppanen, et al. *Movement protein–derived resistance to triple gene block–containing plant viruses.* Journal of General Virology, vol. 78, 1997, pp 1241–1246.

Beck, et al. *Disruption of virus movement confers broad–spectrum resistance against systemic infection by plant viruses with a triple gene block*Plant Biology Acad Sci USA, vol. 91, Oct. 1994, pp 10310–10314.

PCT International Search Report for PCT BE99 00089.

* cited by examiner

*Primary Examiner*—James Ketter
*Assistant Examiner*—David Lambertson
(74) *Attorney, Agent, or Firm*—Knobbe, Martens, Olson & Bear, LLP

(57) ABSTRACT

The present invention concerns a method of genetic modification of a TGB-3 wild type viral sequence for reducing or suppressing the possible deleterious effects of the agronomic properties of a transformed plant or plant cell by the TGB-3 viral sequence, comprising the following successive steps: submitting the sequence to point mutation(s) which allow the substitution of at least one amino-acid into a different amino-acid, selecting genetically modified TGB-3 wild type viral sequences having the point mutation(s) and which are not able to promote cell-to-cell movement of a mutant virus having a dysfunctional TGB-3 wild type viral sequence, when expressed in trans from a replicon, further selecting among the genetically modified TGB-3 viral sequences, the specifically genetically modified sequence which inhibits infection with a co-inoculated wild type virus when the mutant form was expressed from a replicon, and recovering the specifically genetically modified TGB-3 viral sequence.

25 Claims, No Drawings

METHOD OF GENETIC MODIFICATION OF A WILD TYPE VIRAL SEQUENCE

This is the U.S. National Phase under 35 U.S.C. §371 of International Patent Application PCT/BE99/00089, "published in English under PCT Article 21(2)" filed Jul. 9, 1999, which claims priority of European application EP 98870159.5, filed Jul. 10, 1998.

FIELD OF THE INVENTION

The present invention is related to a method of genetic modification of a wild type viral sequence, for reducing or suppressing deleterious properties of plants or plant cells transformed by said wild type viral sequence.

The present invention is also related to the modified viral sequence obtained by said method, and to the plant and the plant cell comprising said modified viral sequence.

BACKGROUND OF THE INVENTION AND STATE OF THE ART

The widespread viral disease of the sugar beet plant (*Beta vulgaris*) called Rhizomania is caused by a furovirus, the beet necrotic yellow vein virus (BNYVV) (1, 2) which is transmitted to the root of the beet by the soilborne fungus *Polymyxa betae* (3).

The disease affects significantly acreages of the area where the sugar beet plant is grown for industrial use in Europe, USA and Japan and is still in extension in several places in Western Europe (4, 5).

Since 1986, number of reports and publications have described the use of isolated viral nucleotidic sequences expressed in plants to confer a high level of tolerance against a specific infectious virus or even to confer a broad spectrum type of resistance against a number of related viruses (6, 7, 8). One of the most documented viral resistance strategies based on genetic engineering, in many cultivated species such as potato, squash, cucumber or tomato, is the use of the viral nucleotidic sequence which under the control of plant regulatory elements, encodes the coat-protein of the target virus (9).

However, in coat-protein mediated resistance, the expression of a certain level of resistance in the transgenic plant might be attributed to different mechanisms such as RNA co-suppression and not necessarily to the production of the protein sequence.

In general, the virus sequence will be transformed in an appropriate cell or tissue culture of the plant species using an Agrobacterium mediated transformation system or a direct gene transfer method according to the constraints of the tissue culture or cell culture method which can be successfully applied in a given species. A whole plant will be regenerated and the expression of the transgene will be characterised.

Though sugar beet is known as a recalcitrant species in cell culture, limiting the extent of practical genetic engineering applications in that species, there are number of isolated reports of successful transformation and regeneration of whole plants (38). A few examples of engineering tolerance to the BNYVV by transforming and expressing the BNYVV coat-protein sequence in the sugar beet genome have also been published (11, WO91/13159) though they rarely report data on whole functional transgenic sugar beet plants (12). In particular, reports show limited data on the level of resistance observed in infected conditions with transgenic sugar beet plants transformed with a gene encoding a BNYVV coat-protein sequence (13, 14).

A complete technology package including a sugar beet transformation method and the use of the expression of the BNYVV coat-protein sequence as a resistance source in the transgenic sugar beet plant obtained by said transformation method has been described in the Patent Application WO91/13159.

Based on the information published, it can not be concluded that the coat-protein mediated resistance mechanism provides any potential for conferring to the sugar beet plant a total immunity to the BNYVV-infection by inhibiting the virus multiplication and diffusion mechanisms completely. To identify a resistance mechanism which significantly blocks the spread of the virus at the early stage of the infection process would be a major criteria of success to develop such a transgenic resistance. In addition, such resistance would diversify the mechanisms of resistance available.

Because the disease is shown to expand in many countries or areas, at a speed depending upon the combination of numerous local environmental and agricultural factors, there is a major interest to diversification and improvement of the genetic resistance mechanisms which may, alone or in combination, confer a stable and long lasting resistance strategy in the current and future varieties of sugar beet plants which are grown for industrial use.

The genome of beet necrotic yellow vein furovirus (BNYVV) consists of five plus-sense RNAs, two of which (RNAs 1 and 2) encode functions essential for infection of all plants while the other three (RNAs 3, 4 and 5) are implicated in vector-mediated infection of sugar beet (*Beta vulgaris*) roots. Cell-to-cell movement of BNYVV is governed by a set of three successive, slightly overlapping viral genes on RNA 2 known as the triple gene block (TGB), which encode, in order, the viral proteins P42, P13 and P15 (gene products are designated by their calculated $M_r$ in kilodalton).

In the following description, the TGB genes and the corresponding proteins will be identified by the following terms: TGB-1, TGB-2, TGB-3 or by their encoded viral protein number P42, P13 and P15. TGB counterparts are present in other furoviruses and in potex-, carla- and hordeiviruses (15, 18, 19, 20, 21 and 22). In the enclosed table 1 are represented viruses having a TGB-3 sequence, the molecular weight of TGB-3 of said viruses, their host and references.

It has been shown previously that independent expression of P15 from a viral-RNA replication species known as a "replicon", derived from BNYVV RNA 3, inhibits infection with BNYVV by interfering cell-to-cell movement (16).

In order to introduce a virus comprising a TGB-3 nucleic acid sequence into a plant cell or a plant, it has been proposed to incorporate a nucleic acid construct comprising said TGB-3 nucleic acid sequence operably linked to one or more regulatory sequences active in said plant (WO98/07875).

However, while expression of wild type TGB-3 viral sequence in a transgenic plant allows the blocking of said viral infection, the presence of said wild type sequence may induce deleterious effects on the agronomic properties of transformed plants or plant cells.

AIMS OF THE INVENTION

The present invention aims to provide a new method for inducing a genetic modification of a wild type viral sequence involved in the multiplication and diffusion mechanisms of virus infecting plants, in order to reduce or suppress the possible deleterious effects upon plants or plant cells transformed by said viral sequence.

Another aim of the present invention is to provide a method to obtain such a modified viral sequence which blocks virus infection when it is incorporated into a plant or a plant cell.

SUMMARY OF THE INVENTION

The present invention is related to a method of genetic modification of a TGB-3 wild type viral sequence, preferably the BNYVV P15 viral sequence, for reducing or suppressing the possible deleterious effects on the agronomic properties of the transformed plants or plant cells by said TGB-3 viral sequence.

Preferably, said genetic modification is a point mutation which allows the substitution of at least one amino-acid into another different amino-acid of said TGB-3 wild type sequence, preferably the substitution of at least one amino-acid into another different amino-acid in the BNYVV P15 sequence.

It seems that the function of the TGB-3 wild type sequence in cell-to-cell movement involves at least in part "bridging" interactions between an element of the host plant (preferably a component of the plasmodesmata), and an element of viral origin (preferably another viral protein involved in cell-to-cell movement). Disruption of either the domain of the TGB-3 wild type sequence (which putatively interacts with the host element) or the domain of the TGB-3 wild type sequence (which putatively interacts with the viral element), allows the inhibition of the cell-to-cell movement.

In addition, it seems that said specific mutations in a TGB-3 wild type sequence allow the production of mutants produced in a transgenic plant, which will still interact with the viral element, but not with the host element. These mutants might compete for binding sites on the viral element of the TGB-3 wild type sequence produced in the initial stage of the viral infection, and abort the infection by inhibiting viral movement to an adjacent cell.

Advantageously, the substitution of at least one amino-acid into another different amino-acid of said sequence is made in regions rich in hydrophilic amino-acids usually present at the surface of the protein in its native configuration.

Preferably, the point mutation(s) allow the substitution of one or two amino-acids into one or two different amino-acids.

In the enclosed Table 1, preferred examples of said viruses having a TGB-3 wild type viral sequence, the molecular weight of the corresponding TGB-3 peptide, their hosts and a reference, are described. The specific wild type P15 nucleotidic and amino-acid sequences of BNYVV are also already described (17).

The above-described point mutations were realised by conventional methods known by the person skilled in the art.

The above mutants containing the point mutation were tested for their ability to promote cell-to-cell movement of a viral mutant (with a dysfunctional TGB-3 sequence, preferably a BNYVV mutant with a dysfunctional P15 gene) when expressed in trans from a replicon. These mutants were incapable of promoting such movement and were tested for their ability to inhibit infection with a co-inoculated wild type TGB-3 virus, preferably co-inoculated with a wild type BNYVV, when the mutant form of the TGB-3 sequence, preferably the P15 gene, was expressed from a replicon.

The Inventors have discovered unexpectedly that the genetic modification method according to the invention (preferably a point mutation) could be used to obtain a modified TGB-3 viral sequence (preferably a modified BNYVV P15 sequence), which is able to block virus infection without producing deleterious effects when incorporated in the genome of a plant or a plant cell.

It is meant by "being able to block viral infection into a plant or a plant cell", the possibility to obtain a high degree of tolerance by the plant or plant cell transformed by said modified TGB-3 viral sequence to said viral infection, in particular the possibility to ensure rapid and total blocking of the virus multiplication and diffusion mechanisms into the plant, preferably the blocking of the BNYVV virus multiplication and diffusion mechanisms into a sugar beet plant (*Beta vulgaris*), including fodder beet, Swiss Whard and table beet which may also be subjected to said BNYVV infection.

Said tolerance or resistance could be easily measured by various methods well known by the person skilled in the art.

Preferably, the genetic modifications in the TGB-3 wild type viral sequence are point mutations in the portions of said wild type viral sequence involved in the mechanisms of viral cell-to-cell movements.

The present invention is also related to the modified TGB-3 viral nucleotidic and amino-acid sequences obtained (recovered) by said (modification and selection) method, more preferably the BNYVV P15 modified nucleotidic and amino-acid sequences obtained (recovered) by said method.

Preferably, said BNYVV P15 nucleotidic and amino-acid sequences are selected from the group consisting of the following nucleotidic (SEQ ID Nos. 1, 3 and 5) or corresponding amino-acid sequences (SEQ ID Nos. 2, 4 and 6):

```
SEQ ID NO 1
ATGGTGCTTGTGGTTGCAGTAGCTTTATCTAATATTGTATTGTACATAGTTGCCGGTTGT    60

SEQ ID NO 2:
M   V   L   V   V   A   V   A   L   S   N   I   V   L   Y   I   V   A   G   C
GTTGTTGTCAGTATGTTGTACTCACCGTTTTTCAGCAACGATGTTAAAGCGTCCAGCTAT   120

V   V   V   S   M   L   Y   S   P   F   F   S   N   D   V   K   A   S   S   Y

GCGGGAGCAATTTTTAAGGGGAGCGGCTGTATCATGGACAGGAATTCGTTTGCTCAATTT   180

A   G   A   I   F   K   G   S   G   C   I   M   D   R   N   S   F   A   Q   F
```

-continued

```
GGGAGTTGCGATATTCCAAAGCATGTAGCCGAGTCCATCACTAAGGTTGCCACCAAAGAG    240
 G   S   C   D   I   P   K   H   V   A   E   S   I   T   K   V   A   T   K   E

CACGATGTTGACATAATGGTAAAAAGGGGTGAAGTGACCGTTCGTGTTGTGACTCTCACC    300
 H   D   V   D   I   M   V   K   R   G   E   V   T   V   R   V   V   T   L   T

GAAACTATTTTTATAATATTATCTAGATTGTTTGGTTTGGCGGTGTTTTTGTTCATGATA    360
 E   T   I   F   I   I   L   S   R   L   P   G   L   A   V   F   L   F   M   I

TGTTTAATGTCTATAGTTTGGTTTTGGTATCATAGATAA                         399
 C   L   M   S   I   V   W   F   W   Y   H   R   *

SEQ ID NO 3:
ATGGTGCTTGTGGTTAAAGTAGATTTATCTAATATTGTATTGTACATAGTTGCCGGTTGT    60

SEQ ID NO 4:
 M   V   L   V   V   K   V   D   L   S   N   I   V   L   Y   I   V   A   G   C

GTTGTTGTCAGTATGTTGTACTCACCGTTTTTCAGCAACGATGTTAAAGCGTCCAGCTAT   120
 V   V   V   S   M   L   Y   S   P   F   F   S   N   D   V   K   A   S   S   Y

GCGGGAGCAATTTTTAAGGGGAGCGGCTGTATCATGGCCGCGAATTCGTTTGCTCAATTT   180
 A   G   A   I   F   K   G   S   G   C   I   M   A   A   N   S   F   A   Q   F

GGGAGTTGCGATATTCCAAAGCATGTAGCCGAGTCCATCACTAAGGTTGCCACCAAAGAG   240
 G   S   C   D   I   P   K   H   V   A   E   S   I   T   K   V   A   T   K   E

CACGATGTTGACATAATGGTAAAAAGGGGTGAAGTGACCGTTCGTGTTGTGACTCTCACC   300
 H   D   V   D   I   M   V   K   R   G   E   V   T   V   R   V   V   T   L   T

GAAACTATTTTTATAATATTATCTAGATTGTTTGGTTTGGCGGTGTTTTTGTTCATGATA   360
 E   T   I   F   I   I   L   S   R   L   F   G   L   A   V   F   L   F   M   I

TGTTTAATGTCTATAGTTTGGTTTTGGTATCATAGATAA                        399
 C   L   M   S   I   V   W   F   W   Y   H   R   *

SEQ ID NO 5:
ATGGTGCTTGTGGTTAAAGTAGATTTATCTAATATTGTATTGTACATAGTTGCCGGTTGT    60

SEQ ID NO: 6
 M   V   L   V   V   K   V   D   L   S   N   I   V   L   Y   I   V   A   G   C

GTTGTTGTCAGTATGTTGTACTCACCGTTTTTCAGCAACGATGTTAAAGCGTCCAGCTAT   120
 V   V   V   S   M   L   Y   S   P   F   F   S   N   D   V   K   A   S   S   Y

GCGGGAGCAATTTTTAAGGGGAGCGGCTGTATCATGGACAGGAATTCGTTTGCTCAATTT   180
 A   G   A   I   F   K   G   S   G   C   I   M   D   R   N   S   F   A   Q   F

GGGAGTTGCGATATTCCAAAGCATGTAGCCGAGTCCATCACTAAGGTTGCCACCAAAGAG   240
 G   S   C   D   I   P   K   H   V   A   E   S   I   T   K   V   A   T   K   E

CACGATGTTGACATAATGGTAAAAAGGGGTGAAGTGACCGTTCGTGTTGTGACTCTCACC   300
 H   D   V   D   I   M   V   K   R   G   E   V   T   V   R   V   V   T   L   T

GAAACTATTTTTATAATATTATCTAGATTGTTTGGTTTGGATGATTTTTTGTTCATGATA   360
 E   T   I   F   I   I   L   S   R   L   F   G   L   D   D   F   L   F   M   I

TGTTTAATGTCTATAGTTTGGTTTTGGTATCATAGATAA                        399
 C   L   M   S   I   V   W   F   W   Y   H   R   *
```

In the following description, the various modified BNYVV TGB-3 sequences will be hereafter called "P15 mutants", identified by the following reference: BNP15-Ala1, corresponding to SEQ ID NO: 1, and SEQ ID NO: 2, BNP15-Ala4 corresponding to SEQ ID NO: 3 and SEQ ID NO: 4, BNP15-Asp9, corresponding to SEQ ID NO: 5 and SEQ ID NO: 6.

The nucleotidic and corresponding amino-acid sequences of SEQ ID NO: 1, SEQ ID NO: 3 and SEQ ID NO: 5 can be compared to SEQ ID NOS: 7 and 8, which are the sequences of the wild type P15 nucleotidic and amino-acid sequence already described (17).

The present invention is also related to the vector comprising said modified nucleotidic sequence possibly being operably linked to one or more regulatory sequence(s) active into a plant or a plant cell. Preferably, said vector is a plasmid comprising already said regulatory sequence(s) active into a plant or a plant cell.

The present invention is also related to a method for inducing a resistance to a virus comprising a TGB-3 sequence, preferably one of the viruses described in the enclosed Table 1, and more preferably the BNYVV virus, said method comprising the following steps:

preparing a nucleic acid construct comprising a nucleic acid sequence being genetically modified according to the method of the invention and being operably linked to one or more regulatory sequences active into a plant or a plant cell, transforming the plant cell with the nucleic acid construct, and possibly regenerating the transgenic plant from the transformed plant cell.

Preferably, said method is used for inducing a resistance to the BNYVV into a sugar beet plant or a sugar beet cell. Said method comprises the following steps:

preparing a nucleic acid construct comprising a modified nucleic acid sequence obtained by the method according to the invention, preferably preparing a nucleic acid construct comprising a nucleic acid sequence selected from the group consisting of SEQ ID NO: 1, SEQ ID NO: 3 or SEQ ID NO: 5, being operably linked to one or more regulatory sequences active into a plant, transforming the sugar beet plant cell with the nucleic acid construct, and possibly regenerating the transgenic sugar beet plant from the transformed sugar beet plant cell.

The present invention is also related to the obtained (recovered) transgenic plant or the transgenic plant cell resistant to an infection by a virus comprising a TGB-3 sequence, preferably one of the viruses described in the enclosed Table 1, more preferably the BNYVV virus, said plant or plant cell comprising a nucleic acid construct having a TGB-3 modified nucleic acid sequence, being operably linked to one or more regulatory sequences capable of being active in a plant or a plant cell.

Preferably, said modified nucleic acid sequence is selected from the group consisting of SEQ ID NO: 1, SEQ ID NO: 3 and SEQ ID NO: 5, being operably linked to one or more regulatory sequences active into a plant or a plant cell.

Preferably, the cell is a stomatal cell and the regulatory sequence comprises a promoter sequence and a terminator sequence capable of being active in a plant. Said promoter sequence can be constitutive or could be obtained from a foreigner promoter sequence, and is preferably selected from the group consisting of the 35S Cauliflower Mosaic Virus promoter, and/or the polyubiquitin *Arabidopsis thaliana* promoter.

Advantageously, the promoter sequence is a promoter which is mainly capable of being active in the root tissue of plants such as the par promoter or the haemoglobin gene from *Perosponia andersonii*.

A last aspect of the present invention is related to a transgenic plant tissue such as fruit, stem, root, tuber, seed of the transgenic plant according to the invention or a reproducible structure (preferably selected from the group consisting of calluses, buds or embryos) obtained from the transgenic plant or the plant cell according to the invention.

The techniques of plant transformation, tissue culture and regeneration used in the method according to the invention are the ones well known by the person skilled in the art. Such techniques are preferably the ones described in the International Patent Applications WO95/101778, WO91/13159 (corresponding to the European Patent Application EP-B-0517833), WO98/07875, which are incorporated herein by reference.

These techniques are preferably used for the preparation of transgenic sugar beet plants and plant cells according to the invention.

REFERENCES

1. Tamada T. & Baba T., *Annals of the Phytopathological Society of Japan* 39, pp. 325–332 (1973)
2. Kuszala M.& Putz C., *Annals of Phytopathology* 9, pp. 435–446 (1977)
3. Keskin B., *Archiv für Mikrobiology* 49, pp. 348–374 (1964)
4. Asher M. J. C., *Rhizomania In The sugar beet crop*, ed. D. A. Cooke and R. K. Scott, Chapman & Hall, London, pp. 312–338 (1993)
5. Richard-Molard M., *Rhizomanie In Institut francais de la betterave industrielle. Compte-rendu des travaux effectués en* 1994, ITB, Paris pp. 225–229 (1995)
6. Powell A. P. et al., *Science* 232, pp. 738–743 (1986)
7. Fritchen J. H. & Beachy R. N., *Ann. Rev. Microbiol.* 47, pp. 739–763 (1993)
8. Wilson T. M. A., *Proc. Natl. Acad. Sci. USA* 90, pp. 3134–3141 (1993)
9. Gonsalves D. & Slightom J. L., *Seminars in Virology* 4, pp. 397–405 (1993)
10. D'Halluin K. et al., *Biotechnology* 10, pp. 309–314 (1992)
11. Kallerhof J. et al., *Plant Cell Reports* 9, pp. 224–228 (1990)
12. Ehlers U. et al., *Theoretical and Applied Genetic* 81, pp. 777–782 (1991)
13. Kraus J. et al., *Field performance of transgenic sugar beet plants expresing BNYVV coat protein plants, Fourth International Congress of Plant Molecular Biology, Int. Soc. for Plant Molecular Biology*, Amsterdam (1994)
14. Maiss E. et al., *Proceedings of the Third International Symposium on the Biosafety Results of Field Tests of Genetically Modified Plants and Microorganisms*, Monterey, pp. 129–139 (1994)
15. Gilmer et al., *Virology* 189, pp. 40–47 (1992)
16. Bleykasten-Grosshans et al., *Mol. Plant-Microbe Interact.* 10, pp. 240–246 (1997)
17. Bouzoubaa et al., *J. Gen. Virol.* 67, pp. 1689–1700 (1986)

18. Richards & Tamada, *Annu. Revendication. Phytopathol.* 30, pp. 291–313 (1992)
19. Bouzoubaa et al., *J. Gen. Virol.* 68, pp. 615–626 (1987)
20. Herzog et al., *J. Gen. Virol.* 18, pp. 3147–3155 (1994)
21. Scott et al., *J. Gen. Virol.* 75, pp. 3561–3568 (1994)
22. Koonin & Dolja, *Crit. Revendication. Biochem. and Mol. Biol.* 28, pp. 375–430 (1993)

TABLE 1

| Virus | Size of TGB-3 | Host | Reference |
|---|---|---|---|
| Apple stem pitting virus | 8 kDa | apple | Jelkman, J. Gen. Virol. 75, 1535–1542 (1994) |
| Blueberry scorch virus | 7 kDa | blueberry | Cavileer et al., J. Gen. Virol. 75, 711–720 (1994) |
| Potato virus M | 7 kDa | potato | Zavriev et al., J. Gen. Virol. 72, 9–14 (1991) |
| White clover mosaic virus | 8 kDa | clover | Forster et al., Nucl. Acids Res. 16, 291–303 (1988) |
| Cymbidium mosaic virus | 10 kDa | orchid | Neo et al., Plant Mol. Biol. 18, 1027–1029 (1992) |
| Potato virus X | 8 kDa | potato | Rupasov et al., J. Gen. Virol. 70, 1861–1869 (1994) |
| Barley stripe mosaic virus | 17 kDa | barley | Gustafson et al., Nucl. Acids Res. 14, 3895–3909 (1986) |
| Potato mop top virus | 21 kDa | potato | Scott et al., J. Gen. Virol. 75, 3561–3568 (1994) |
| Peanut clump virus | 17 kDa | peanut | Herzog et al., J. Gen. Virol. 75, 3147–3155 (1994) |
| Beet soil-borne virus | 22 kDa | Sugar beet | Koenig et al., Virology 216, 202–207 (1996) |

What is claimed is:

1. A method of identifying mutants in a triple gene block 3 (TGB-3) viral sequence which inhibit infection of a virus into a cell, comprising:

mutating said TGB-3 sequence;

selecting TGB-3 mutants which no longer promote cell-to-cell movement of a (TGB-3 minus) mutant virus when expressed in trans from a replicon;

further selecting from the identified mutants those which also inhibit infection with a co-inoculated wild type virus when the mutant TGB-3 is expressed from a replicon;

recovering said mutant TGB-3 viral sequence wherein a mutant TGB-3 sequence recovered from the foregoing selection steps is a mutant TGB-3 viral sequence that inhibits infection of a virus into a cell.

2. The method according to claim 1, wherein the TGB-3 wild type viral sequence is the beet necrotic yellow vein virus (BNYVV) P15 sequence.

3. A genetically modified TGB-3 viral sequence comprising the sequence of SEQ ID NO:3.

4. A vector comprising the genetically modified TGB-3 viral sequence encoding to claim 3.

5. The vector of claim 4 operably linked to one or more regulatory sequence(s) active in a plant cell.

6. A method for inducing resistance to a virus in a plant or a plant cell comprising:

preparing a nucleic acid construct comprising a genetically modified TGB-3 viral sequence according to claim 3 operably linked to one or more regulatory sequence(s) active in a plant or a plant cell, and transforming a plant cell with said nucleic acid construct, thereby inducing resistance to a virus in a plant or plant cell.

7. The method according to claim 6, wherein the virus is selected from the group consisting of the apple stem pitting virus, the blueberry scorch virus, the potato virus M, the white clover mosaic virus, the *Cymbidium* mosaic virus, the barley stripe mosaic virus, the potato mop top virus, the peanut clump virus, the beet soil-borne virus and the BNYVV virus.

8. The method according to claim 6 wherein the plant cell is a stomatal cell.

9. The method according to claim 6 wherein the plant is selected from the group consisting of apple, blueberry, potato, clover, orchid, barley, peanut and sugar beet.

10. The method of claim 6 further comprising regenerating a transgenic plant from the transformed plant cell.

11. The method according to claim 6, wherein the regulatory sequence comprises a promoter sequence or a terminator sequence active in a plant.

12. The method according to claim 11, wherein the promoter sequence is a constitutive or a foreign promoter sequence.

13. The method according to claim 11, wherein the promoter sequence is selected from the group consisting of the 35S Cauliflower Mosaic Virus promoter, the polyubiquitin *Arabidopsis thaliana* promoter, and both promoters.

14. The method according to claim 11, wherein the promoter sequence is a promoter active in the root tissue of plants.

15. The method of claim 14, wherein said promoter active in the root tissue of plants is the par promoter of the haemoglobin gene from *Perospomia andersonii*.

16. A transgenic plant or transgenic plant cell resistant to a virus comprising a nucleic acid construct having a genetically modified TGB-3 viral sequence according to claim 3 operably linked to one or more regulatory sequence(s) active in a plant or a plant cell.

17. A transgenic plant or transgenic plant cell according to claim 16, wherein the virus is selected from the group consisting of the apple stem pitting virus, the blueberry scorch virus, the potato virus M, the white clover mosaic virus, the *Cymbidium* mosaic virus, the potato virus X, the barley stripe mosaic virus, the potato mop top virus, the peanut clump virus, the beet soil-borne virus and the BNYVV virus.

18. The transgenic plant or transgenic plant cell according to claim 16, wherein the regulatory sequence comprises a promoter sequence and a terminator sequence active in a plant.

19. A transgenic plant tissue from the transgenic plant or comprising the transgenic plant cell of claim 16 wherein said tissue is selected from the group consisting of fruit, stem, root, tuber, and seed.

20. The transgenic plant or transgenic plant cell according to claim 16 selected from the group consisting of apple, blueberry, potato, clover, orchid, barley, peanut and sugar beet.

21. The transgenic plant of claim 20, wherein said promoter active in the root tissue of plants is the par promoter of the haemoglobin gene from *Perosponia andersonii*.

22. The transgenic plant or transgenic plant cell according to claim 20, wherein said transgenic plant is sugar beet or transgenic sugar beet cell.

23. The transgenic plant or transgenic plant cell according to claim 16, wherein the regulatory sequence(s) comprise a promoter sequence which is a constitutive or a foreign vegetal promoter sequence.

24. The transgenic plant or transgenic plant cell according to claim 23, wherein the promoter is selected from the group consisting of the 35S Cauliflower Mosaic Virus promoter, the polyubiquitin *Arabidopsis thaliana* promoter, and both.

25. The transgenic plant or transgenic plant cell according to claim 23 wherein promoter sequence is active in root tissues.

* * * * *

UNITED STATES PATENT AND TRADEMARK OFFICE
CERTIFICATE OF CORRECTION

| | | |
|---|---|---|
| PATENT NO. | : 6,835,538 B1 | Page 1 of 1 |
| APPLICATION NO. | : 09/743905 | |
| DATED | : December 28, 2004 | |
| INVENTOR(S) | : Lauber et al. | |

It is certified that error appears in the above-identified patent and that said Letters Patent is hereby corrected as shown below:

On column 19 of Claims, in Claim 4, line 24, delete "encoding" and insert --according--, therefor.
On Column 20 of Claims, in Claim 15, line 10, delete "Perospomia" and insert --Perosponia--, therefor.
On Column 20 of Claims, in Claim 24, line 48, after "promoter" insert --sequence--.
On Column 20 of Claims, in Claim 25, line 51, after "wherein" insert —the--.

Signed and Sealed this

Fifth Day of September, 2006

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 399
<212> TYPE: DNA
<213> ORGANISM: Artificial Sequence
<220> FEATURE:
<223> OTHER INFORMATION: genetically modified TGB-3 viral sequence
<220> FEATURE:
<221> NAME/KEY: CDS
<222> LOCATION: (1)...(399)

<400> SEQUENCE: 1 atg gtg ctt gtg gtt gca gta gct tta tct aat att gta ttg tac ata      48
Met Val Leu Val Val Ala Val Ala Leu Ser Asn Ile Val Leu Tyr Ile
1               5                   10                  15 gtt gcc ggt tgt gtt gtt gtc agt atg ttg tac tca ccg ttt ttc agc      96
Val Ala Gly Cys Val Val Val Ser Met Leu Tyr Ser Pro Phe Phe Ser
            20                  25                  30 aac gat gtt aaa gcg tcc agc tat gcg gga gca att ttt aag ggg agc     144
Asn Asp Val Lys Ala Ser Ser Tyr Ala Gly Ala Ile Phe Lys Gly Ser
        35                  40                  45 ggc tgt atc atg gac agg aat tcg ttt gct caa ttt ggg agt tgc gat     192
Gly Cys Ile Met Asp Arg Asn Ser Phe Ala Gln Phe Gly Ser Cys Asp
    50                  55                  60 att cca aag cat gta gcc gag tcc atc act aag gtt gcc acc aaa gag     240
Ile Pro Lys His Val Ala Glu Ser Ile Thr Lys Val Ala Thr Lys Glu
65                  70                  75                  80
```

-continued

```
cac gat gtt gac ata atg gta aaa agg ggt gaa gtg acc gtt cgt gtt      288
His Asp Val Asp Ile Met Val Lys Arg Gly Glu Val Thr Val Arg Val
                85                  90                  95 gtg act ctc acc gaa act att ttt ata ata tta tct aga ttg ttt ggt      336
Val Thr Leu Thr Glu Thr Ile Phe Ile Ile Leu Ser Arg Leu Phe Gly
            100                 105                 110 ttg gcg gtg ttt ttg ttc atg ata tgt tta atg tct ata gtt tgg ttt      384
Leu Ala Val Phe Leu Phe Met Ile Cys Leu Met Ser Ile Val Trp Phe
        115                 120                 125 tgg tat cat aga taa                                                  399
Trp Tyr His Arg *
    130
```

<210> SEQ ID NO 2
<211> LENGTH: 132
<212> TYPE: PRT
<213> ORGANISM: Artificial Sequence
<220> FEATURE:
<223> OTHER INFORMATION: genetically modified TGB-3 viral sequence

<400> SEQUENCE: 2

```
Met Val Leu Val Val Ala Val Ala Leu Ser Asn Ile Val Leu Tyr Ile
1               5                   10                  15

Val Ala Gly Cys Val Val Ser Met Leu Tyr Ser Pro Phe Phe Ser
            20                  25                  30

Asn Asp Val Lys Ala Ser Ser Tyr Ala Gly Ala Ile Phe Lys Gly Ser
        35                  40                  45

Gly Cys Ile Met Asp Arg Asn Ser Phe Ala Gln Phe Gly Ser Cys Asp
    50                  55                  60

Ile Pro Lys His Val Ala Glu Ser Ile Thr Lys Val Ala Thr Lys Glu
65                  70                  75                  80

His Asp Val Asp Ile Met Val Lys Arg Gly Glu Val Thr Val Arg Val
                85                  90                  95

Val Thr Leu Thr Glu Thr Ile Phe Ile Ile Leu Ser Arg Leu Phe Gly
            100                 105                 110

Leu Ala Val Phe Leu Phe Met Ile Cys Leu Met Ser Ile Val Trp Phe
        115                 120                 125

Trp Tyr His Arg
    130
```

<210> SEQ ID NO 3
<211> LENGTH: 399
<212> TYPE: DNA
<213> ORGANISM: Artificial Sequence
<220> FEATURE:
<223> OTHER INFORMATION: genetically modified TGB-3 viral sequence
<220> FEATURE:
<221> NAME/KEY: CDS
<222> LOCATION: (1)...(399)

<400> SEQUENCE: 3

```
atg gtg ctt gtg gtt aaa gta gat tta tct aat att gta ttg tac ata       48
Met Val Leu Val Val Lys Val Asp Leu Ser Asn Ile Val Leu Tyr Ile
1               5                   10                  15 gtt gcc ggt tgt gtt gtt gtc agt atg ttg tac tca ccg ttt ttc agc       96
Val Ala Gly Cys Val Val Val Ser Met Leu Tyr Ser Pro Phe Phe Ser
            20                  25                  30 aac gat gtt aaa gcg tcc agc tat gcg gga gca att ttt aag ggg agc      144
Asn Asp Val Lys Ala Ser Ser Tyr Ala Gly Ala Ile Phe Lys Gly Ser
        35                  40                  45
```

```
ggc tgt atc atg gcc gcg aat tcg ttt gct caa ttt ggg agt tgc gat      192
Gly Cys Ile Met Ala Ala Asn Ser Phe Ala Gln Phe Gly Ser Cys Asp
     50                  55                  60 att cca aag cat gta gcc gag tcc atc act aag gtt gcc acc aaa gag      240
Ile Pro Lys His Val Ala Glu Ser Ile Thr Lys Val Ala Thr Lys Glu
 65              70                  75                  80 cac gat gtt gac ata atg gta aaa agg ggt gaa gtg acc gtt cgt gtt      288
His Asp Val Asp Ile Met Val Lys Arg Gly Glu Val Thr Val Arg Val
                 85                  90                  95 gtg act ctc acc gaa act att ttt ata ata tta tct aga ttg ttt ggt      336
Val Thr Leu Thr Glu Thr Ile Phe Ile Ile Leu Ser Arg Leu Phe Gly
             100                 105                 110 ttg gcg gtg ttt ttg ttc atg ata tgt tta atg tct ata gtt tgg ttt      384
Leu Ala Val Phe Leu Phe Met Ile Cys Leu Met Ser Ile Val Trp Phe
         115                 120                 125 tgg tat cat aga taa                                                   399
Trp Tyr His Arg  *
    130

<210> SEQ ID NO 4
<211> LENGTH: 132
<212> TYPE: PRT
<213> ORGANISM: Artificial Sequence
<220> FEATURE:
<223> OTHER INFORMATION: genetically modified TGB-3 viral sequence

<400> SEQUENCE: 4

Met Val Leu Val Val Lys Val Asp Leu Ser Asn Ile Val Leu Tyr Ile
 1               5                  10                  15

Val Ala Gly Cys Val Val Ser Met Leu Tyr Ser Pro Phe Phe Ser
             20                  25                  30

Asn Asp Val Lys Ala Ser Ser Tyr Ala Gly Ala Ile Phe Lys Gly Ser
             35                  40                  45

Gly Cys Ile Met Ala Ala Asn Ser Phe Ala Gln Phe Gly Ser Cys Asp
     50                  55                  60

Ile Pro Lys His Val Ala Glu Ser Ile Thr Lys Val Ala Thr Lys Glu
 65              70                  75                  80

His Asp Val Asp Ile Met Val Lys Arg Gly Glu Val Thr Val Arg Val
                 85                  90                  95

Val Thr Leu Thr Glu Thr Ile Phe Ile Ile Leu Ser Arg Leu Phe Gly
             100                 105                 110

Leu Ala Val Phe Leu Phe Met Ile Cys Leu Met Ser Ile Val Trp Phe
         115                 120                 125

Trp Tyr His Arg
    130

<210> SEQ ID NO 5
<211> LENGTH: 399
<212> TYPE: DNA
<213> ORGANISM: Artificial Sequence
<220> FEATURE:
<223> OTHER INFORMATION: genetically modified TGB-3 viral sequence
<220> FEATURE:
<221> NAME/KEY: CDS
<222> LOCATION: (1)...(399)

<400> SEQUENCE: 5 atg gtg ctt gtg gtt aaa gta gat tta tct aat att gta ttg tac ata       48
Met Val Leu Val Val Lys Val Asp Leu Ser Asn Ile Val Leu Tyr Ile
 1               5                  10                  15
```

```
gtt gcc ggt tgt gtt gtt gtc agt atg ttg tac tca ccg ttt ttc agc      96
Val Ala Gly Cys Val Val Val Ser Met Leu Tyr Ser Pro Phe Phe Ser
            20                  25                  30 aac gat gtt aaa gcg tcc agc tat gcg gga gca att ttt aag ggg agc     144
Asn Asp Val Lys Ala Ser Ser Tyr Ala Gly Ala Ile Phe Lys Gly Ser
        35                  40                  45 ggc tgt atc atg gac agg aat tcg ttt gct caa ttt ggg agt tgc gat     192
Gly Cys Ile Met Asp Arg Asn Ser Phe Ala Gln Phe Gly Ser Cys Asp
 50                  55                  60 att cca aag cat gta gcc gag tcc atc act aag gtt gcc acc aaa gag     240
Ile Pro Lys His Val Ala Glu Ser Ile Thr Lys Val Ala Thr Lys Glu
 65                  70                  75                  80 cac gat gtt gac ata atg gta aaa agg ggt gaa gtg acc gtt cgt gtt     288
His Asp Val Asp Ile Met Val Lys Arg Gly Glu Val Thr Val Arg Val
                 85                  90                  95 gtg act ctc acc gaa act att ttt ata ata tta tct aga ttg ttt ggt     336
Val Thr Leu Thr Glu Thr Ile Phe Ile Ile Leu Ser Arg Leu Phe Gly
            100                 105                 110 ttg gat gat ttt ttg ttc atg ata tgt tta atg tct ata gtt tgg ttt     384
Leu Asp Asp Phe Leu Phe Met Ile Cys Leu Met Ser Ile Val Trp Phe
        115                 120                 125 tgg tat cat aga taa                                                 399
Trp Tyr His Arg  *
130

<210> SEQ ID NO 6
<211> LENGTH: 132
<212> TYPE: PRT
<213> ORGANISM: Artificial Sequence
<220> FEATURE:
<223> OTHER INFORMATION: genetically modified TGB-3 viral sequence

<400> SEQUENCE: 6

Met Val Leu Val Val Lys Val Asp Leu Ser Asn Ile Val Leu Tyr Ile
 1               5                  10                  15

Val Ala Gly Cys Val Val Val Ser Met Leu Tyr Ser Pro Phe Phe Ser
            20                  25                  30

Asn Asp Val Lys Ala Ser Ser Tyr Ala Gly Ala Ile Phe Lys Gly Ser
        35                  40                  45

Gly Cys Ile Met Asp Arg Asn Ser Phe Ala Gln Phe Gly Ser Cys Asp
 50                  55                  60

Ile Pro Lys His Val Ala Glu Ser Ile Thr Lys Val Ala Thr Lys Glu
 65                  70                  75                  80

His Asp Val Asp Ile Met Val Lys Arg Gly Glu Val Thr Val Arg Val
                 85                  90                  95

Val Thr Leu Thr Glu Thr Ile Phe Ile Ile Leu Ser Arg Leu Phe Gly
            100                 105                 110

Leu Asp Asp Phe Leu Phe Met Ile Cys Leu Met Ser Ile Val Trp Phe
        115                 120                 125

Trp Tyr His Arg
130

<210> SEQ ID NO 7
<211> LENGTH: 399
<212> TYPE: DNA
<213> ORGANISM: Beet Necrotic Yellow Vein Virus
<220> FEATURE:
<221> NAME/KEY: CDS
<222> LOCATION: (1)...(399)
<223> OTHER INFORMATION: Nucleotide sequence of BNYVV RNA-2 encoding P15
      protein
```

```
<400> SEQUENCE: 7 atg gtg ctt gtg gtt aaa gta gat tta tct aau att gta ttg tac ata    48
Met Val Leu Val Val Lys Val Asp Leu Ser Asn Ile Val Leu Tyr Ile
 1               5                  10                  15 gtt gcc ggt tgt gtt gtt gtc agt atg ttg tac tca ccc ttt ttc agc    96
Val Ala Gly Cys Val Val Val Ser Met Leu Tyr Ser Pro Phe Phe Ser
             20                  25                  30 aac gat gtt aaa gcg tcc agc tat gcg gga gca att ttt aag ggg agc   144
Asn Asp Val Lys Ala Ser Ser Tyr Ala Gly Ala Ile Phe Lys Gly Ser
         35                  40                  45 ggc tgt atc atg gac agg aat tcg ttt gct caa ttt ggg agt tgc gat   192
Gly Cys Ile Met Asp Arg Asn Ser Phe Ala Gln Phe Gly Ser Cys Asp
     50                  55                  60 att cca aag cat gta gcc gag tcc atc act aag gtt gcc acc aaa gag   240
Ile Pro Lys His Val Ala Glu Ser Ile Thr Lys Val Ala Thr Lys Glu
 65                  70                  75                  80 cac gat gtt gac ata atg gta aaa agg ggt gaa gtc acc gtt cgt gtt   288
His Asp Val Asp Ile Met Val Lys Arg Gly Glu Val Thr Val Arg Val
                 85                  90                  95 gtg act ctc acc gaa act att ttt ata ata tta tct aga ttg ttt ggt   336
Val Thr Leu Thr Glu Thr Ile Phe Ile Ile Leu Ser Arg Leu Phe Gly
            100                 105                 110 ttg gcg gtg ttt ttg ttc atg ata tgt tta atg tct ata gtt tgg ttt   384
Leu Ala Val Phe Leu Phe Met Ile Cys Leu Met Ser Ile Val Trp Phe
        115                 120                 125 tgg tat cat aga taa                                               399
Trp Tyr His Arg  *
    130

<210> SEQ ID NO 8
<211> LENGTH: 132
<212> TYPE: PRT
<213> ORGANISM: Beet Necrotic Yellow Vein Virus
<220> FEATURE:
<223> OTHER INFORMATION: Protein encoded by SEQ ID NO:7

<400> SEQUENCE: 8

Met Val Leu Val Val Lys Val Asp Leu Ser Asn Ile Val Leu Tyr Ile
 1               5                  10                  15

Val Ala Gly Cys Val Val Val Ser Met Leu Tyr Ser Pro Phe Phe Ser
             20                  25                  30

Asn Asp Val Lys Ala Ser Ser Tyr Ala Gly Ala Ile Phe Lys Gly Ser
         35                  40                  45

Gly Cys Ile Met Asp Arg Asn Ser Phe Ala Gln Phe Gly Ser Cys Asp
     50                  55                  60

Ile Pro Lys His Val Ala Glu Ser Ile Thr Lys Val Ala Thr Lys Glu
 65                  70                  75                  80

His Asp Val Asp Ile Met Val Lys Arg Gly Glu Val Thr Val Arg Val
                 85                  90                  95

Val Thr Leu Thr Glu Thr Ile Phe Ile Ile Leu Ser Arg Leu Phe Gly
            100                 105                 110

Leu Ala Val Phe Leu Phe Met Ile Cys Leu Met Ser Ile Val Trp Phe
        115                 120                 125

Trp Tyr His Arg
    130
```